United States Patent [19]

Cope

[11] Patent Number: 4,834,727
[45] Date of Patent: May 30, 1989

[54] EYE DROPPER BOTTLE ATTACHMENT FOR POST-SURGICAL AND GENERAL USE

[76] Inventor: Samuel M. Cope, 265 Western Promenade, Portland, Me. 04102

[21] Appl. No.: 129,987

[22] Filed: Dec. 8, 1987

[51] Int. Cl.$^4$ ........................................... A61M 35/00
[52] U.S. Cl. ..................................................... 604/300
[58] Field of Search ................................. 604/294–302

[56] References Cited

U.S. PATENT DOCUMENTS

| | | | |
|---|---|---|---|
| 2,722,216 | 11/1955 | Robbins | 604/302 |
| 3,058,466 | 10/1962 | Routsong | 604/302 |
| 3,598,121 | 8/1971 | Lelicoff | 604/302 |
| 3,872,866 | 3/1975 | Lelicoff | 604/302 |
| 4,002,168 | 1/1977 | Petterson | 604/302 |
| 4,085,750 | 4/1978 | Bosshold | 128/233 |
| 4,257,417 | 3/1981 | Gibilisco | 604/302 |
| 4,543,096 | 9/1985 | Keene | 604/300 |
| 4,605,398 | 8/1986 | Herrick | 604/302 |
| 4,685,906 | 8/1987 | Murphy | 604/300 |

FOREIGN PATENT DOCUMENTS

| | | | |
|---|---|---|---|
| 0594860 | 3/1934 | Fed. Rep. of Germany | 604/302 |
| 0722852 | 9/1931 | France | 604/302 |
| 1025304 | of 1953 | France . | |
| 2142829A | of 1985 | United Kingdom . | |

Primary Examiner—C. Fred Rosenbaum
Assistant Examiner—Denise Whelton

[57] ABSTRACT

An eye dropper dispenser bottle attachment for post-surgical and general use for preventing contact between a dispenser and surgical areas and insuring safe, accurate convenient placement of eye drops which comprises a generally oval ring contoured to fit the periorbital area, at least one post extending upwardly from the ring, a second ring mounted on the upper end of the post, the latter being discontinuous to define a bottle neck gripping opening for receiving and holding the neck of an inverted eye drop bottle. Adjacent parts of the discontinuous ring are resiliently mechanically separable to enlarge the opening for reception and removal of the bottle and to resiliently grip the bottle when released. Preferably the attachment includes a pair of such posts extending upwardly from opposite lateral sides of the oval ring, one part of the discontinuous ring being mounted on the upper end of each post, the parts facing each other to define the opening and the posts resilient and capable of being mechanically spread apart thereby to enlarge said opening for reception and retraction of a bottle neck, said two parts gripping and holding said bottle neck when not so spread.

12 Claims, 4 Drawing Sheets

EYE DROPPER BOTTLE ATTACHMENT FOR POST-SURGICAL AND GENERAL USE

This invention relates to instruments for holding plastic squeeze bottles to assist in the dispensing of medications and cleansing solutions by the drop or spray method onto the human eye.

BACKGROUND OF THE INVENTION

A variety of devices for accomplishing this purpose have been previously proposed. An example includes U.S. Pat. No. 2,898,911 which discloses a resilient eye cup capable of being snapped onto the shoulder of an eye drop bottle. U.S. Pat. No. 3,058,466 is directed to a bridge-like member arranged to hold a bottle, positioning being accomplished by placing the feet of the bridge above and below the eye. Still another prior art proposal appears in U.S. Pat. No. 3,872,866 which teaches threading a positioning device to the threads of a bottle neck. U.S. Pat. No. 4,085,750 shows resilient arms extending from a collar fitting the bottle's neck, the idea being that the arms are engaged with the closed eyelid and allowed to spread to hold the lid open. French Pat. No. 1,025,304, published Apr. 14, 1953 also discloses the use of arms but with the additional feature of rupturing the drop container when the arms are squeezed to release a fluid. It is clear that any device of this kind employing individual arms is dangerous when in use, having the potential for injuring the patient's eye.

It is the object of the present invention to provide a safe instrument which is easily and quickly attached to a plastic eye dropper bottle to increase accuracy in dispensing ophthalmic solutions in post-surgical and general use.

SUMMARY OF THE INVENTION

In accordance with the invention there is provided an eye dropper dispenser bottle attachment for post-surgical and general use for preventing contact between a dispenser and surgical areas and insuring safe, accurate convenient placement of eye drops which comprises a generally oval ring contoured to fit the periorbital area, at least one post extending upwardly from the oval ring, a second ring mounted on the upper end of the post, the latter ring being discontinuous to define a bottle neck gripping opening for receiving and holding the neck of an inverted eye dropper bottle.

In one preferred embodiment a pair of posts extend upwardly from opposite sides of the oval ring, one part of the discontinuous ring being mounted on the upper end of each post, the parts facing each other defining the opening and the posts being resilient and capable of being mechanically spread apart thereby to enlarge the opening for reception and retraction of a bottle neck, the said two parts gripping and holding the bottle neck when not so spread.

In another preferred embodiment the discontinuous ring comprises a hook, which may or may not be resilient, adapted to releasably receive and grip the neck of an eye dropper bottle. Preferably, the post is vertically adjustable and the hook laterally adjustable and in all cases the oval ring is provided with indicia indicating its proper orientation when in use. Where more than one post is employed the posts are preferably concave toward the center of the attachment to facilitate reception and retraction of an eye dropper bottle cap when the bottle is positioned in said attachment. For some uses the oval ring in the several embodiments may be reduced in size and adapted to fit within the orbital area of the eye.

Still further objects, features and advantages of the invention will become apparent from the following detailed description of presently preferred embodiments of the same taken in connection with the accompanying drawings.

Description of Preferred Embodiments

Figure 1:
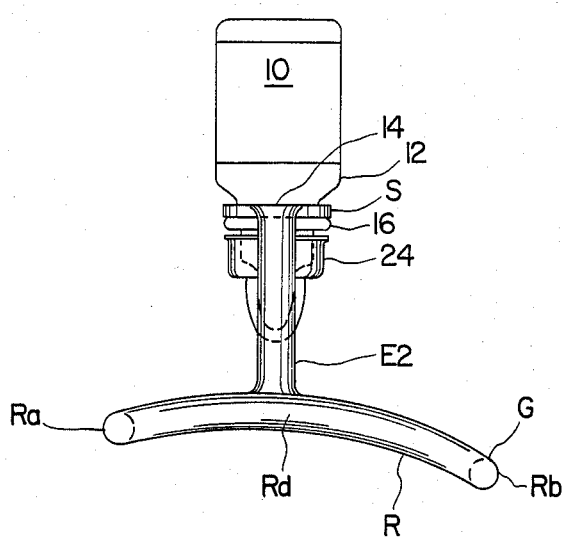
FIG. 1 is a front view of one preferred embodiment of the invention.

Plastic dispenser bottles for ophthalmic solutions are made in assorted sizes. Some have regular size spiral threads 18 and nozzle 20, while others have a long body, wider spirals yet usually the same size nozzle. The latter type of bottle is at least ¼" longer from the base of the neck 16 to the nozzle tip 20.

The embodiments described below fit securely that part of the neck 14 of the bottle 10 which is located between the shoulder 12 and the base of the neck 16.

The remaining bottle parts are referred to as nozzle aperture 22 and cap 24.

Figure 2:
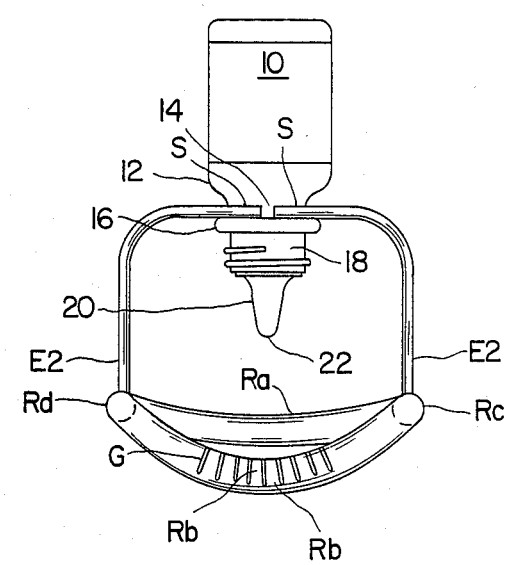
FIG. 2 is an end view of the same.

The embodiment shown in FIGS. 1 and 2 is a split ring attachment. Rim R is contoured to fit the periorbital area, with the rim at Rc and Rd concave at the bottom. Two posts E2, one attached to the upper part of rim at Rc, and the other to the lower part of rim at Rd, are positioned slightly toward the medial aspect of the rim, Ra. Posts E2 are concave at the inner mid-surface and converge towards the center at the top ends. Rather than straight converging posts, concave posts are used to retain flexibility and to allow for maximum available space in which to remove the bottle cap 24. The top ends of posts E2 support a rigid split ring S.

FIG. 1 is a front view with post E2 on lower rim at Rd. The split ring S engages the neck of bottle 14 above the base of neck 16 and below the shoulder 12 of bottle.

FIG. 2 is a correctly positioned dispenser bottle. To place bottle into position, the operator grasps the upper part of both posts E2 and pulls firmly in opposite directions to enlarge the area within the split ring S. The inverted bottle is inserted such that neck 14 is firmly grasped by split ring S. Posts E2 have sufficient flexibility and tension to permit the split ring S to grip bottle neck 14 tightly.

The bottle 10 with nozzle tip 20 is now in the proper and safe position, high enough above the rim surface to avoid contact with any part of the eye.

Figure 3:
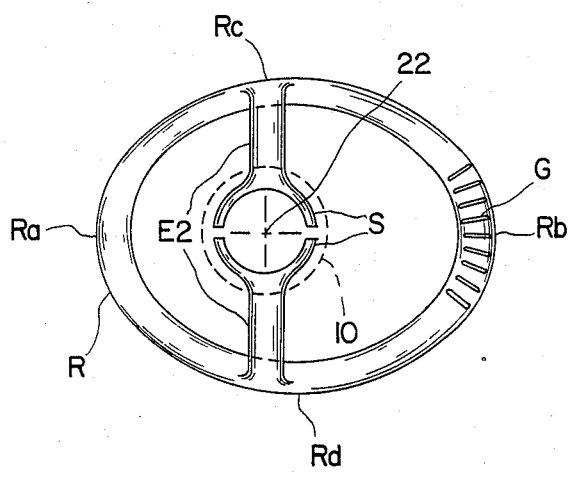
FIG. 3 is a plan view thereof.

FIG. 3 is a top plan view of the split ring embodiment with parts relatively positioned. The bottle 10, nozzle aperture 22 and cross grooves G are shown. Grooves G, which act as indicia to indicate placement direction to the user, should face outward. The assembled unit is rotated 180° to properly position for use on the opposite side of face.

Figure 4:
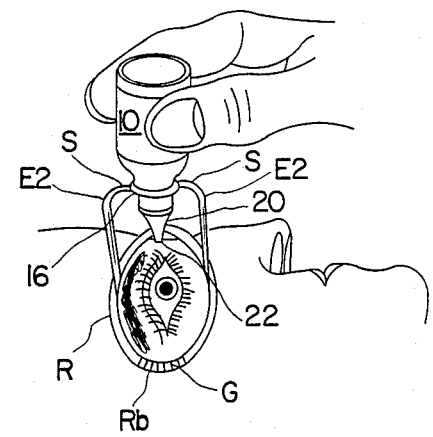
FIG. 4 a perspective view showing this embodiment in use.

FIG. 4 is a perspective view (not to scale) of the same embodiment correctly positioned for use. In use, cap 24 is removed. With the patient's head tilted back as far as possible or with the patient in a prone position, the body of bottle 10 is held with thumb and forefinger and with cross grooves G toward the outer side of face, the instrument is brought toward the eye. Rim R should be positioned with three areas of contact: (1) upper part of rim Rc above the supraorbital ridge; (2) lower part of rim Rd below the infraorbital ridge; and (3) medial part of rim Ra touching the side of the bridge of the nose.

With the patient's eyelids open as far as possible, the body of bottle 10 is gently squeezed with thumb and forefinger to deposit one or more drops onto the eye. The instrument is then rotated a half turn, the same reference areas being used to position it to service the other eye. The cap 24 may be replaced and the bottle stored with the instrument attached.

Figure 5:
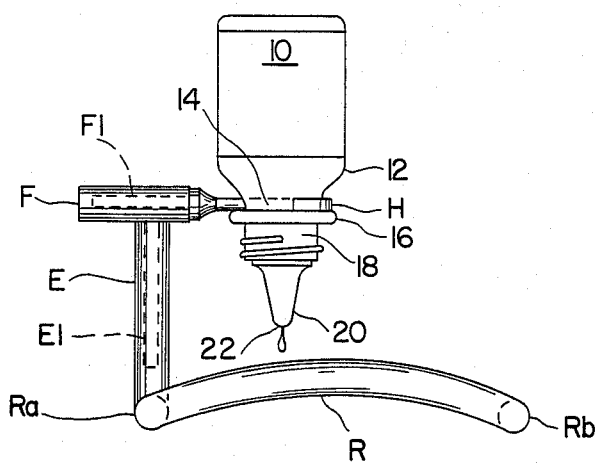
FIG. 5 is a front view of a second embodiment of the invention.
Figure 6:
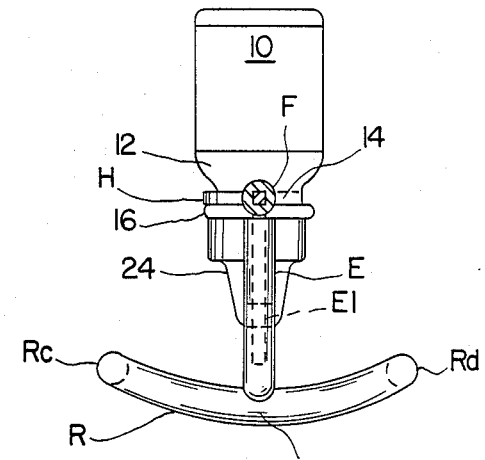
FIG. 6 is an end view of the same.

FIGS. 5 and 6 illustrate a hook ring embodiment. This embodiment has the same rim as the previously described instrument. Vertical post E at the medial surface of rim Ra extends up to support the horizontal post F from which extends a short rigid arm and hook ring H. The latter is positioned horizontally and equidistant from upper rim Rc and lower rim Rd, and eccentrically toward the medial to permit the bottle 10 and nozzle tip 20 to be correctly positioned. Cross grooves G on rim Rb are also present on this attachment to act as indicia for orientation purposes.

All posts (E, F or E2) are easily made to be extendable when a friction grip is formed if the surface of the post is a tube (female), as in E and F, and the inner part is a shaft (male), as in E1 and F1; or, with the use of oblique spiral threading. If properly shaped, rotation of the tube and shaft is precluded.

Figure 7:
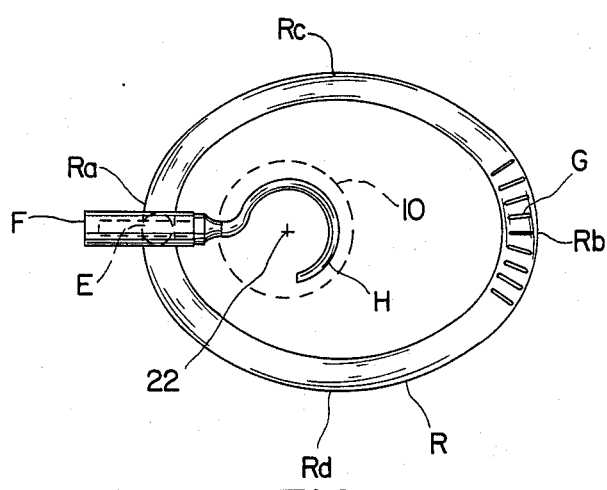
FIG. 7 is a plan view thereof.

FIG. 7 is a plan view of this hook ring embodiment.

To attach the hook ring instrument to a dispenser bottle, the hook ring H and its horizontal post F are securely grasped, the bottle 10 inverted and its neck 14 pressed into hook ring H. With bottle firmly attached, instrument is ready for use as described in connection with FIG. 4.

Figure 9:
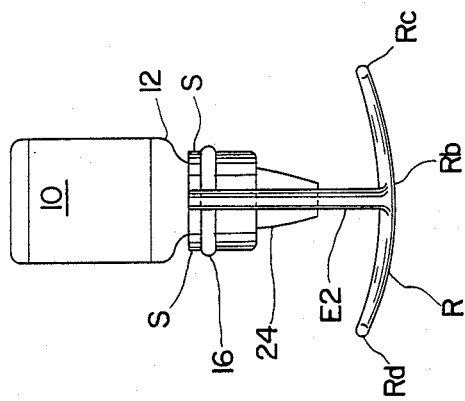
FIG. 9 is an end view of the same.
Figure 8:
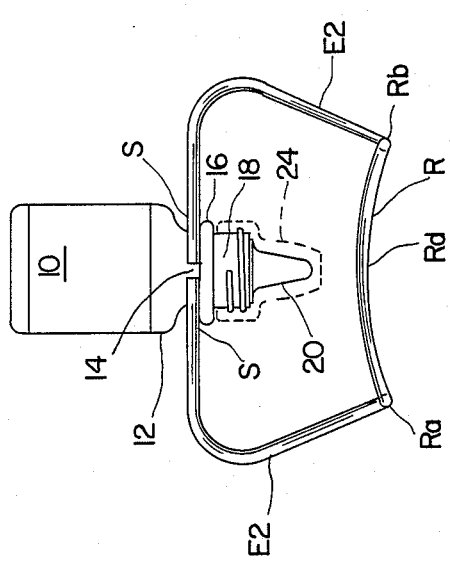
FIG. 8 is a front view of still another embodiment of the invention.

FIGS. 8 and 9 illustrate a further embodiment with a small rim R which fits within the orbital area. The posts' design and appearance are similar to that of the posts in FIGS. 1 and 2 except that here, posts E2 are placed on rim R at Ra and Rb. The split ring S is aligned within the center area of rim R to bring the dispenser bottle 10 and nozzle 20 into the center of the rim and high enough over the eye area to avoid contact. Placement of the bottle into the instrument is as described for the embodiment of FIG. 2.

Figure 10:
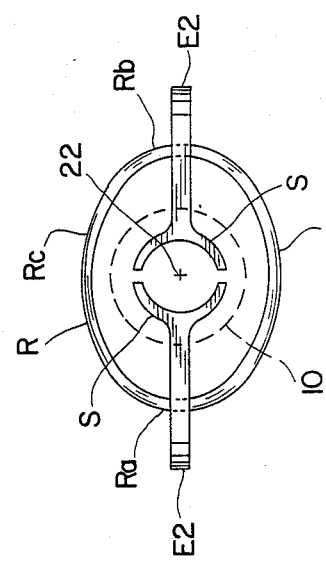
FIG. 10 is a plan view thereof.

FIG. 10 is a plan view detailing position of posts E2 and split ring S inside of rim R.

Figure 11:
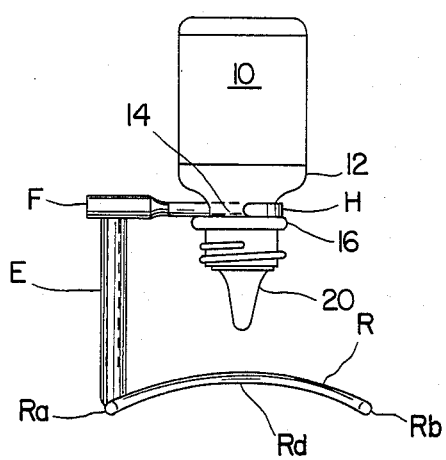
FIG. 11 is a front view of a fourth embodiment of the invention.
Figure 12:
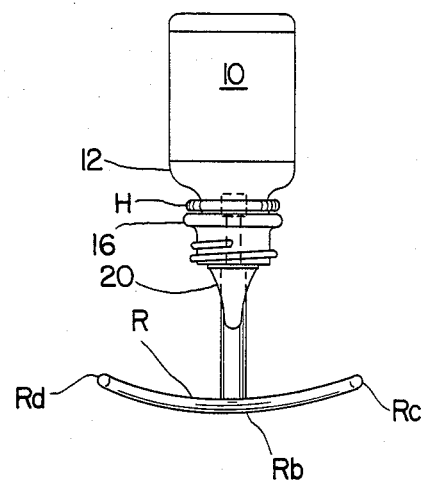
FIG. 12 is an end view of the same.

FIGS. 11 and 12 are front and end views of still another embodiment which consists of a small rim R and a vertical post E which is attached at Ra. The horizontal post F has an extension of a hook ring H which is located in the center of the rim. The attachment of this instrument is as describes for the embodiment of FIG. 7.

Figure 13:
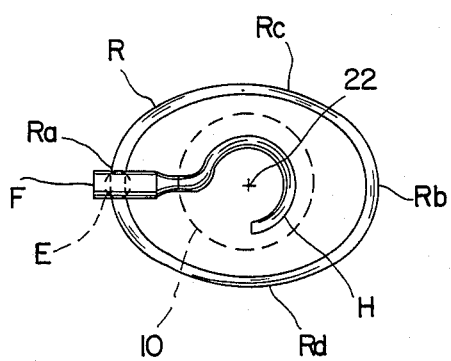
FIG. 13 is a plan view thereof.

FIG. 13 is a plan view of the parts relatively positioned.

Figure 14:
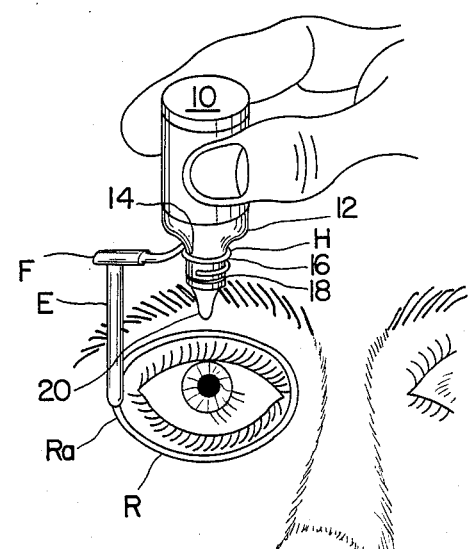
FIG. 14 is a perspective view showing this embodiment in use.

FIG. 14 is a perspective view of a hook ring H instrument positioned for use. Cap 24 is first removed. With the patient's head tilted back as far as possible or the patient in a prone position, the body of bottle 10 is grasped with thumb and forefinger. With vertical post E toward lateral surface of eye and with eye open, lower portion of rim is positioned for contact just below lashes of lower eyelid. The eyelid is gently depressed with the rim to form a cul-de-sac. The instrument is seated by rotating the lower rim which permits the upper rim to gently touch the open upper lid. Blinking reflexes may thus be controlled. The bottle is squeezed to expel solution onto eye. The same technique is used on both eyes.

It will be seen that each form of the invention comprises an instrument which is easily attached to plastic eye dropper bottles to increase accuracy and safety while dispensing ophthalmic solutions in post-surgical and general use. Other features and benefits of this invention are as follows: (a) Permits ease and safety in use of a bottle in the orbital area, by leaving surgically involved areas of the eye undisturbed; (b) directs bottle's nozzle tip to proper height and position over the eye to prevent accidental contact with eye; (c) prevents nozzle tip from contacting sources of contamination; (d) avoids waste of solution by directing deposit of solution to correct spot; (e) when modified for direct application to eyelids, retracts lower eyelid and minimizes blinking reflexes; and (f) provides stability by assisting the elderly or incapacitated in effective application of solutions.

For use in general care, the embodiment of this invention with a smaller oval rim is applied directly to the eyelids. After similar attachment methods are followed, this device assists in deflecting the lower lid and minimizes involuntary blinking.

These devices of the invention are of simple mechanical design, compact for easy packaging and storage, and safe and easy to use. Additionally, they are inexpensive to produce from standard plastic materials such as polyethylene, polypropylene, metal, or a combination of both plastic and metal.

Many changes in details of the above described embodiments are easily introduced without altering the benefits of this invention which will provide individuals with an easy, safe and sanitary means to maintaining post-surgical and general eye care. It is therefore intended that the scope of the invention be limited only by the proper interpretation of the appended claims.

I claim:
1. An eye dropper dispenser bottle attachment apparatus for post-surgical and general use for preventing contact between a dispenser and surgical areas, and for insuring safe, accurate, convenient placement of eye drops from an inverted eye dropper bottle, said attachment comprising:
 a generally oval ring contoured to fit around the eye of a patient lying in a prone position;
 post means extending upwardly from said oval ring mounted thereon;
 second ring means mounted on said post means distant from said oval ring;
 said second ring means being generally circular and comprising at least one arcuate ring portion defin- ing an eye dropper bottle neck receiving opening, said second ring means being generally horizontal when said apparatus is in use with a generally prone patient, said second ring means having an inner diameter which substantially securely fits the neck of an inverted eye dropper bottle so as to engage and firmly grasp within it that part of the bottle's neck located between the shoulder and the neck's base so as to position the nozzle tip thereof substantially centered above and at the proper predetermined distance from the eye when said oval ring is fitted to a patient's eye, said second ring having at least one segment defining said ring which is sufficiently resilient to facilitate releasable reception of said neck therewithin, said post means being offset from the axis of said second ring to provide maximum space wherein to remove and replace a cap on said nozzle when said bottle is held in said second ring;

vertical adjustment means adapted to adjust the vertical position of said post means; and lateral adjustment means adapted to adjust the lateral position of said post means.

2. The attachment of claim 1 wherein said post means comprises a pair of posts extending upwardly from opposite sides of said oval ring, one arcuate ring portion being mounted on the upper end of each post, said portions facing each other to define said opening and the posts being resilient and capable of being mechanically spread apart thereby to enlarge said opening for reception and retraction of a bottle neck, said two portions defining said inner diameter for engaging and grasping said bottle neck when not so spread.

3. The attachment of claim 2 including means permitting vertical adjustment of said posts.

4. The attachment of claim 2 wherein said oval ring is provided with indicia indicating its proper orientation when in use.

5. The attachment of claim 2 wherein said posts are concave toward the center of the attachment to facilitate access to the nozzle of an eye dropper bottle when the bottle is positioned in said attachment.

6. The attachment of claim 2 wherein said oval ring is reduced in size and adapted to fit within the orbital area of the eye.

7. The attachment of claim 1 wherein said oval ring is provided with indicia indicating its proper orientation when in use.

8. The attachment of claim 1 wherein said oval ring is of reduced size so as to fit within the orbital area of the eye.

9. The attachment of claim 1 wherein said oval ring is of enlarged size so as to fit against the periorbital area around the eye.

10. The attachment claimed in claim 1 having a single post means and wherein said second ring is generally hook-shaped.

11. The attachment claimed in claim 1 wherein said post means comprises two posts each of which has an arcuate segment of said second ring mounted thereon.

12. The attachment claimed in claim 11 wherein said two posts are positioned opposite to each other on said oval ring.

* * * * *